US007035688B2

(12) United States Patent
Kast et al.

(10) Patent No.: US 7,035,688 B2
(45) Date of Patent: Apr. 25, 2006

(54) LAMINATE OF MAGNETIC MATERIAL AND METHOD OF MAKING

(75) Inventors: John E. Kast, Hugo, MN (US); Steve T. Deininger, Savage, MN (US); Charles E. Peters, Blaine, MN (US); Jeffrey J. Clayton, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 10/836,116

(22) Filed: Apr. 30, 2004

(65) Prior Publication Data

US 2005/0246001 A1  Nov. 3, 2005

(51) Int. Cl.
*A61N 1/375* (2006.01)
(52) U.S. Cl. .................. 607/36; 336/84 M; 607/61
(58) Field of Classification Search .................. 607/36, 607/61, 29, 34; 336/84 M; 29/830
See application file for complete search history.

(56) References Cited

U.S. PATENT DOCUMENTS

| 3,357,434 | A | 12/1967 | Abell |
| 3,888,260 | A | 6/1975 | Fischell |
| 4,041,955 | A | 8/1977 | Kelly et al. |
| 4,071,032 | A | 1/1978 | Schulman |
| 4,134,408 | A | 1/1979 | Brownlee et al. |
| 4,186,749 | A | 2/1980 | Fryer |
| 5,279,292 | A | 1/1994 | Baumann et al. |
| 5,314,457 | A | 5/1994 | Jeutter et al. |
| 5,411,537 | A | 5/1995 | Munshi et al. |
| 5,468,210 | A | 11/1995 | Matsui et al. |
| 5,527,348 | A | 6/1996 | Winkler et al. |
| 5,562,714 | A | 10/1996 | Grevious |
| 5,613,935 | A | 3/1997 | Jarvik |
| 5,690,693 | A | 11/1997 | Wang et al. |
| 5,713,939 | A | 2/1998 | Nedungadi et al. |
| 5,733,313 | A | 3/1998 | Barreras, Sr. et al. |
| 5,861,019 | A | 1/1999 | Sun et al. |
| 6,067,474 | A | 5/2000 | Schulman et al. |
| 6,154,677 | A | 11/2000 | Leysieffer |
| 6,178,353 | B1 | 1/2001 | Griffith et al. |
| 6,275,737 | B1 | 8/2001 | Mann |
| 6,308,101 | B1 | 10/2001 | Faltys et al. |
| 6,324,430 | B1 | 11/2001 | Zarinetchi et al. |

(Continued)

FOREIGN PATENT DOCUMENTS

EP          0 269 200          6/1988

(Continued)

OTHER PUBLICATIONS

Medtronic, Inc. "Implantable Neurostimulation Systems", 1998.

(Continued)

*Primary Examiner*—Mark Bockelman
*Assistant Examiner*—Eric Bertram
(74) *Attorney, Agent, or Firm*—IPLM Group, P.A.

(57) ABSTRACT

A laminate having a plurality of layers of magnetic material sandwiched together having a first side and a second side and a method of making the laminate. The plurality of layers of magnetic material having a plurality of radial grooves. A first insulative layer applied over the first side of the plurality of layers of magnetic material. A lead wire applied to over first insulative layer at a predetermined location on the first side of the plurality of layers of magnetic material. A second insulative layer applied to the first side of the plurality of layers of magnetic material over the lead wire. A third insulative layer applied to the second side of the plurality of layers of magnetic material. Thus, the laminate is ready to receive a coil.

23 Claims, 21 Drawing Sheets

U.S. PATENT DOCUMENTS

| | | |
|---|---|---|
| 6,505,077 B1 * | 1/2003 | Kast et al. .................... 607/61 |
| 6,516,227 B1 | 2/2003 | Meadows et al. |
| 6,542,777 B1 * | 4/2003 | Griffith et al. ................ 607/57 |
| 6,850,803 B1 * | 2/2005 | Jimenez et al. ............... 607/61 |
| 6,931,713 B1 * | 8/2005 | Roshen ........................ 29/609 |
| 2003/0076211 A1 * | 4/2003 | Matsuta et al. ............ 336/200 |
| 2004/0064175 A1 | 4/2004 | Lessar et al. |

FOREIGN PATENT DOCUMENTS

| | | |
|---|---|---|
| EP | 0 499 939 A1 | 2/1992 |
| EP | 0 499 939 B1 | 2/1992 |
| EP | 0 540 483 | 5/1993 |
| EP | 0 811 395 A2 | 12/1997 |
| EP | 0 811 395 A3 | 12/1997 |
| EP | 1 048 324 A2 | 11/2000 |
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/83029 A1 | 11/2001 |
| WO | WO 01/97908 A2 | 12/2001 |
| WO | WO 01/97908 A3 | 12/2001 |
| WO | WO2004/030751 | 4/2004 |
| WO | WO 2004/030751 | 4/2004 |

OTHER PUBLICATIONS

Sinha, Gunjan, "The Heart, Medicine & Health", Popular Science, p. 43, Feb. 2000.

Medtronic, Inc. "Mattrix Neurostimulation System", Brochure, 1995.

* cited by examiner

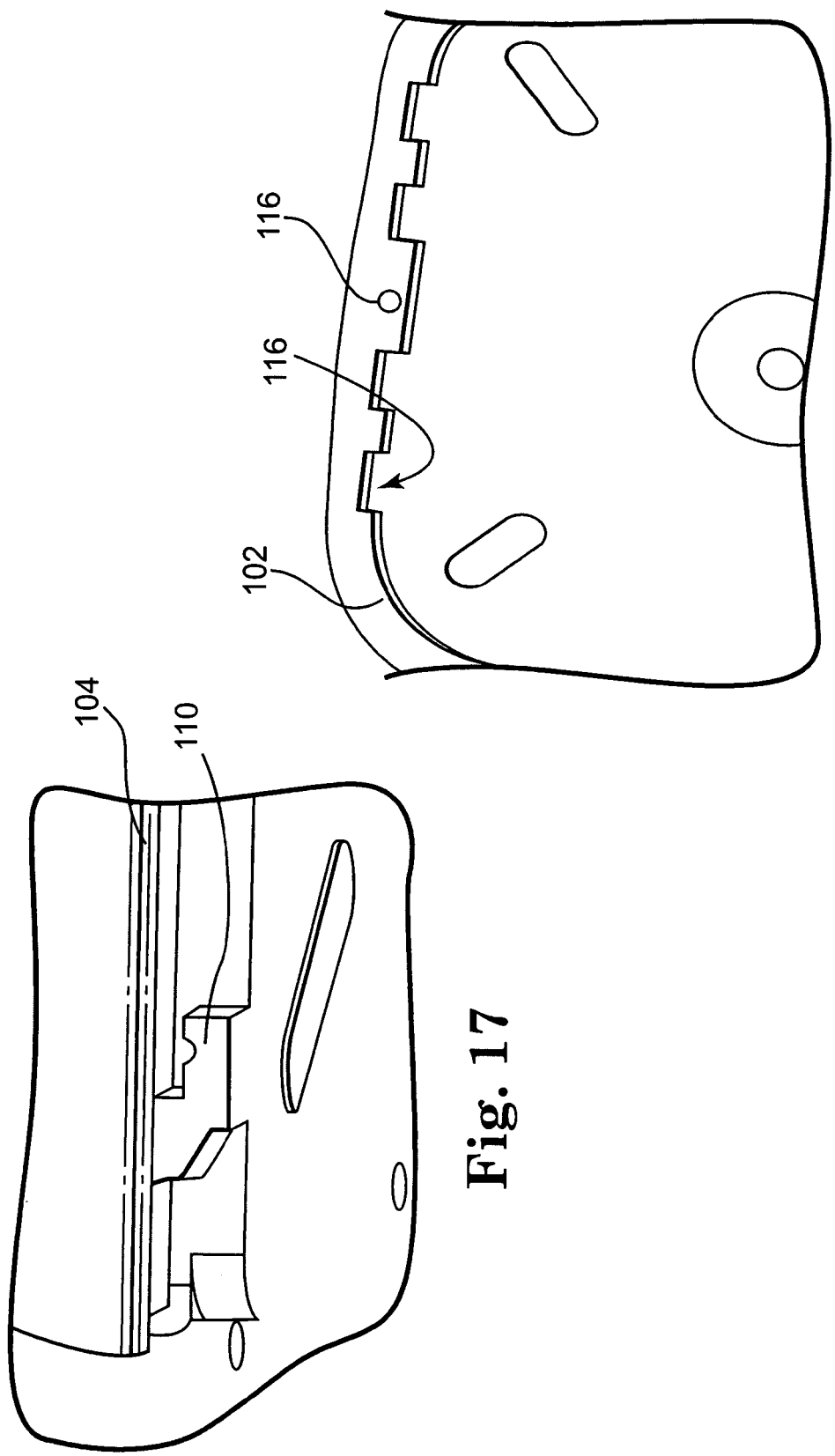

LAMINATE OF MAGNETIC MATERIAL AND METHOD OF MAKING

FIELD OF THE INVENTION

The present invention relates generally to a method of laminating material and, more particularly, to a method of laminating magnetic material, particularly those used in implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Some of these devices, if not all, and other devices either provide an electrical output or otherwise contain electrical circuitry to perform their intended function.

Such implantable medical devices, when implanted, are subjected to a harsh environment in contact with bodily fluids. Such bodily fluids can be corrosive to the implantable medical device. Typically, implantable medical devices are hermetically sealed, often in a titanium case, in order to protect the implantable medical device from the harmful effects of the bodily fluids with which the implantable medical device comes into contact.

The securing of an implantable medical device against infiltration of body fluids which may compromise the integrity and/or reliability of the implantable medical device can lead to very tight tolerances in construction and/or assembly and rigid positioning and fastening of components within the housing of the implantable medical device. Any breach of an otherwise hermetically sealed case could lead to infiltration of body fluids into the implantable medical device and possibly result in a premature failure of the device.

This problem is exacerbated in newer electrically stimulating devices utilizing recharging technology where the implanted secondary coil and electrical contacts are located outside of the titanium case. The problem is further exacerbated by an increase in the number of excitation electrodes for use in patient therapy, therefore resulting in an increase in the number of electrical connections made outside of the titanium case. With the implanted secondary coil and the greater number of electrical contacts located outside of the titanium case, the greater the problem of making a secure, reliable connection without risking compromise of the implantable medical device and possible subsequent premature failure. Failure of an implanted medical device could lead not only to necessary surgery to explant the device but could jeopardize the patient's well being by making the therapeutic advantages of the medical device unavailable to the patient until explantation and re-implantation could occur.

Components used in implantable medical devices are often laminated with protective cover sheets or polymeric sheets as a step in protecting the components against the infiltration of body fluids. While such lamination is often effective at protecting such components, such components may need to be later installed, attached or connected to other components in an implantable medical device. As an example, it may be necessary to electrically connect a laminated article or material to an electrical component that is later mounted on that article. The electrical connection, if not the mechanical connection, may breach the previously created lamination creating a weak spot or a point of possible infiltration of body fluids.

BRIEF SUMMARY OF THE INVENTION

Thus, there is needed a reliable and effective laminated material and a method of making such material, particularly a magnetic material, such as that used with an electrical wire coil, that can be securely electrically connected to a component in a subsequent assembly procedure. The subsequent assembly procedure, including an electrical connection should not unnecessarily compromise the advantages of lamination previously obtained and should provide for improved electrical reliability.

In one embodiment, the present invention provides a laminate having a plurality of layers of magnetic material sandwiched together having a first side and a second side. The plurality of layers of magnetic material having a plurality of radial grooves. A first insulative layer applied over the first side of the plurality of layers of magnetic material. A lead wire applied to over first insulative layer at a predetermined location on the first side of the plurality of layers of magnetic material. A second insulative layer applied to the first side of the plurality of layers of magnetic material over the lead wire. A third insulative layer applied to the second side of the plurality of layers of magnetic material. Thus, the laminate is ready to receive a coil.

In another embodiment, the present invention provides a method of making a laminate. A plurality of layers of magnetic material are sandwiched together. A plurality of radial grooves are created in the plurality of layers of magnetic material. A first insulative layer is applied over the first side of the plurality of layers of magnetic material. A lead wire is applied over the first insulative layer at a predetermined location on the first side of the plurality of layers of magnetic material. A second insulative layer is applied to the first side of the plurality of layers of magnetic material over the lead wire. Thus, the laminate is ready to receive a coil.

In a preferred embodiment, a third insulative layer is applied to the second side of the plurality of layers of magnetic material.

In a preferred embodiment, each of the first insulative layer, the second insulative layer and the third insulative layer comprises a polymer.

In a preferred embodiment, the third insulative layer is adhesively applied.

In a preferred embodiment, the plurality of layers of magnetic material are sandwiched together with intervening adhesive layers.

In a preferred embodiment, the lead wire is adhesively applied.

In a preferred embodiment, the second insulative layer is adhesively applied to the first side of the first insulative layer over the lead wire.

BRIEF DESCRIPTION OF THE DRAWINGS

FIG. 17 is another detailed view of an engagement tab for an internal antenna;

FIG. 18 is a top view of a portion of a housing for implantable medical device illustrating bottom rail engagement and fill hole;

DETAILED DESCRIPTION OF THE INVENTION

Figure 1:
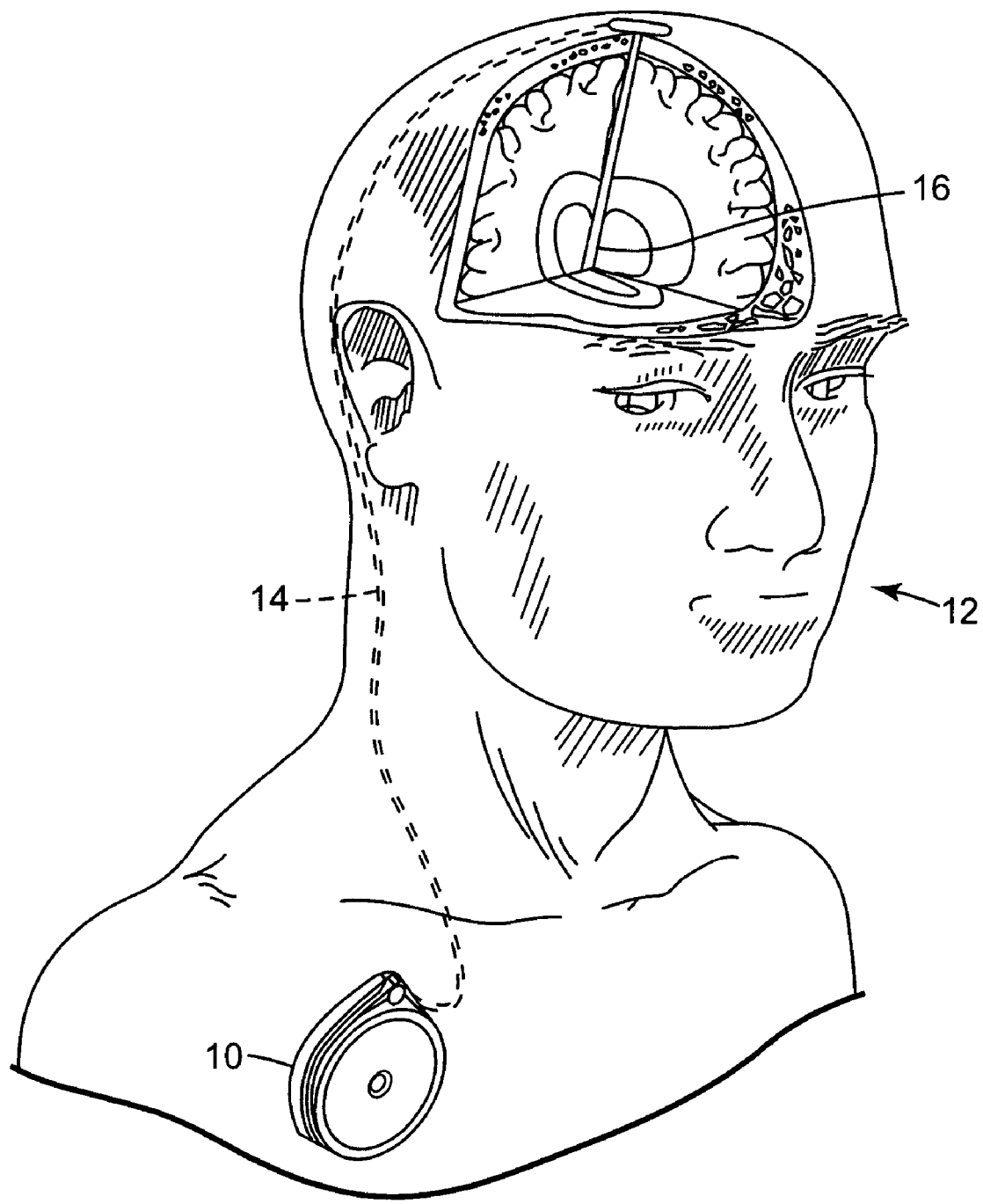
FIG. 1 illustrates an implantable medical device implanted in a patient.

FIG. 1 shows implantable medical device 10 for example, a drug pump, implanted in patient 12. The implantable medical device 10 is typically implanted by a surgeon in a sterile surgical procedure performed under local, regional, or general anesthesia. Before implanting the medical device 10, a catheter 14 is typically implanted with the distal end position at a desired location, or therapeutic delivery site 16, in the body of patient 12 and the proximal end tunneled under the skin to the location where the medical device 10 is to be implanted. Implantable medical device 10 is generally implanted subcutaneously at depths, depending upon application and device 10, of from 1 centimeter (0.4 inches) to 2.5 centimeters (1 inch) where there is sufficient tissue to support the implanted system. Once medical device 10 is implanted into the patient 12, the incision can be sutured closed and medical device 10 can begin operation.

Implantable medical device 10 operates to infuse a therapeutic substance into patient 12. Implantable medical device 10 can be used for a wide variety of therapies such as pain, spasticity, cancer, and many other medical conditions.

The therapeutic substance contained in implantable medical device 10 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Implantable medical device 10 can be any of a number of medical devices such as an implantable pulse generator, implantable therapeutic substance delivery device, implantable drug pump, cardiac pacemaker, cardioverter or defibrillator, as examples.

Electrical power for implantable medical device 10 can be contained in implantable medical device itself. Power source for implantable medical device 10 can be any commonly known and readily available sources of power such as a chemical battery, electrical storage device, e.g., capacitor, a mechanical storage device, e.g., spring, or can be transcutaneously supplied in real time, or some combination.

In order to achieve a transcutaneous transfer of energy, either to charge or recharge an implanted battery or to supply real time power supply, or some combination, an inductive charging technique using an external primary coil and an internal secondary coil can be utilized.

Figure 2:
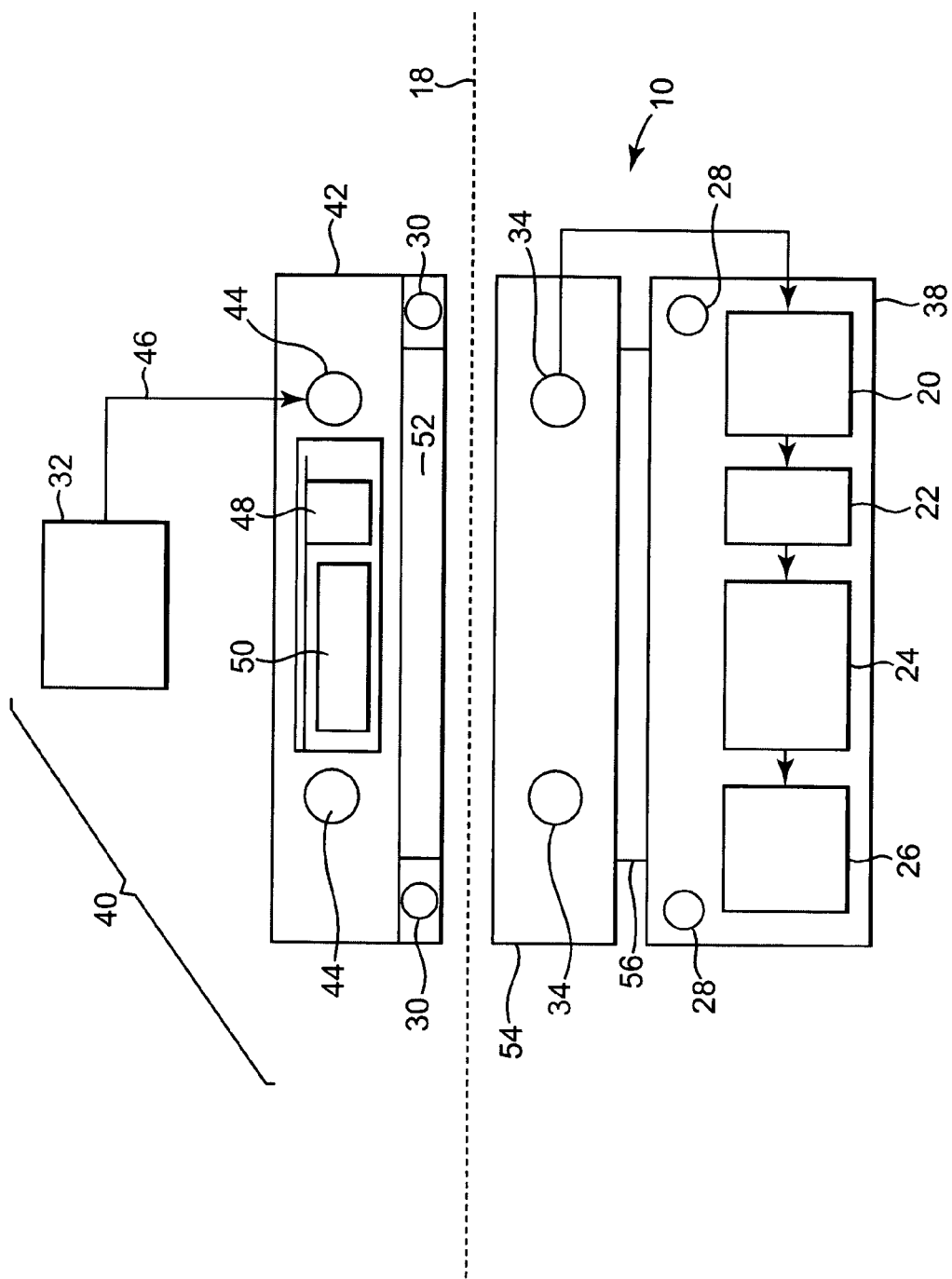
FIG. 2 is a block diagram of an implantable medical device illustrating energy transfer from an external charging device.

FIG. 2 illustrates an embodiment of implantable medical device 10 situated under cutaneous boundary 18. Charging regulation module 20 controls the charging of rechargeable power source 22. Power source 22 powers electronics module 24 which, in turn, controls therapy module 26. Again, charging regulation and therapy control is conventional. Implantable medical device 10 also has internal telemetry coil 28 configured in conventional manner to communicate through external telemetry coil 44 to an external programming device (not shown), charging unit 32 or other device in a conventional manner in order to both program and control implantable medical device and to externally obtain information from implantable medical device 10 once implantable medical device has been implanted. Internal telemetry coil 28, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 56 is positioned between secondary charging coil 34 and housing 38 and sized to cover the footprint of secondary charging coil 34.

Internal telemetry coil 28, having a larger diameter than secondary coil 34, is not completely covered by magnetic shield 56 allowing implantable medical device 10 to communicate with the external programming device with internal telemetry coil 28 in spite of the presence of magnetic shield 56.

Rechargeable power source 24 can be charged while implantable medical device 10 is in place in a patient through the use of external charging device 40. In a preferred embodiment, external charging device 40 consists of charging unit 32 and external antenna 42. Charging unit 32 contains the electronics necessary to drive primary coil 44 with an oscillating current in order to induce current in secondary coil 34 when primary coil 44 is placed in the proximity of secondary coil 34. Charging unit 32 is operatively coupled to primary coil by cable 46. In an alternative embodiment, charging unit 32 and external antenna 42 may be combined into a single unit. Antenna 42 may also optionally contain external telemetry coil 30 which may be operatively coupled to charging unit 32 if it is desired to communicate to or from implantable medical device 10 with external charging device 40. Alternatively, external antenna 42 may optionally contain external telemetry coil 30 which can be operatively coupled to an external programming device, either individually or together with external charging unit 32.

Repositionable magnetic core 48 can help to focus electromagnetic energy from primary coil 30 to more closely be aligned with secondary coil 34. Energy absorptive material 50 can help to absorb heat build-up in external antenna 42 which will also help allow for a lower temperature in implantable medical device 10 and/or help lower recharge times. Thermally conductive material 52 is positioned covering at least a portion of the surface of external antenna 42 which contacts cutaneous boundary 18 of patient 12. Thermally conductive material 52 is positioned on the surface of external charging device 40 in order to distribute any heat which may be generated by external charging device 40.

Secondary coil 34 is located in internal antenna 54 that is separable from housing 38. Magnetic shield 56 is positioned between secondary coil 34 and housing 38 and inside the diameter of internal telemetry coil 28 to help isolate the remainder of implantable medical device 10 from electromagnetic energy from external charging device 40.

Figure 3:
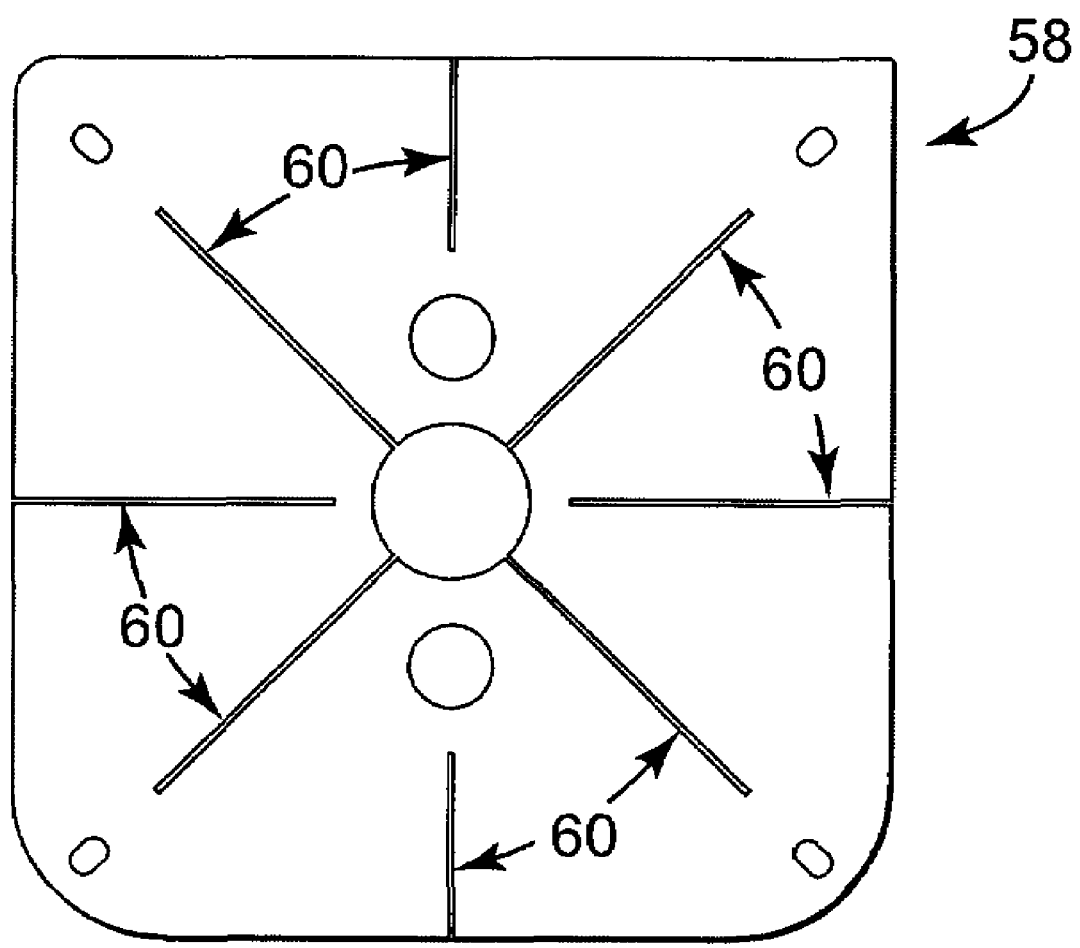
FIG. 3 is a top view of a base laminate used in an internal antenna in an implantable medical device.
Figure 4:
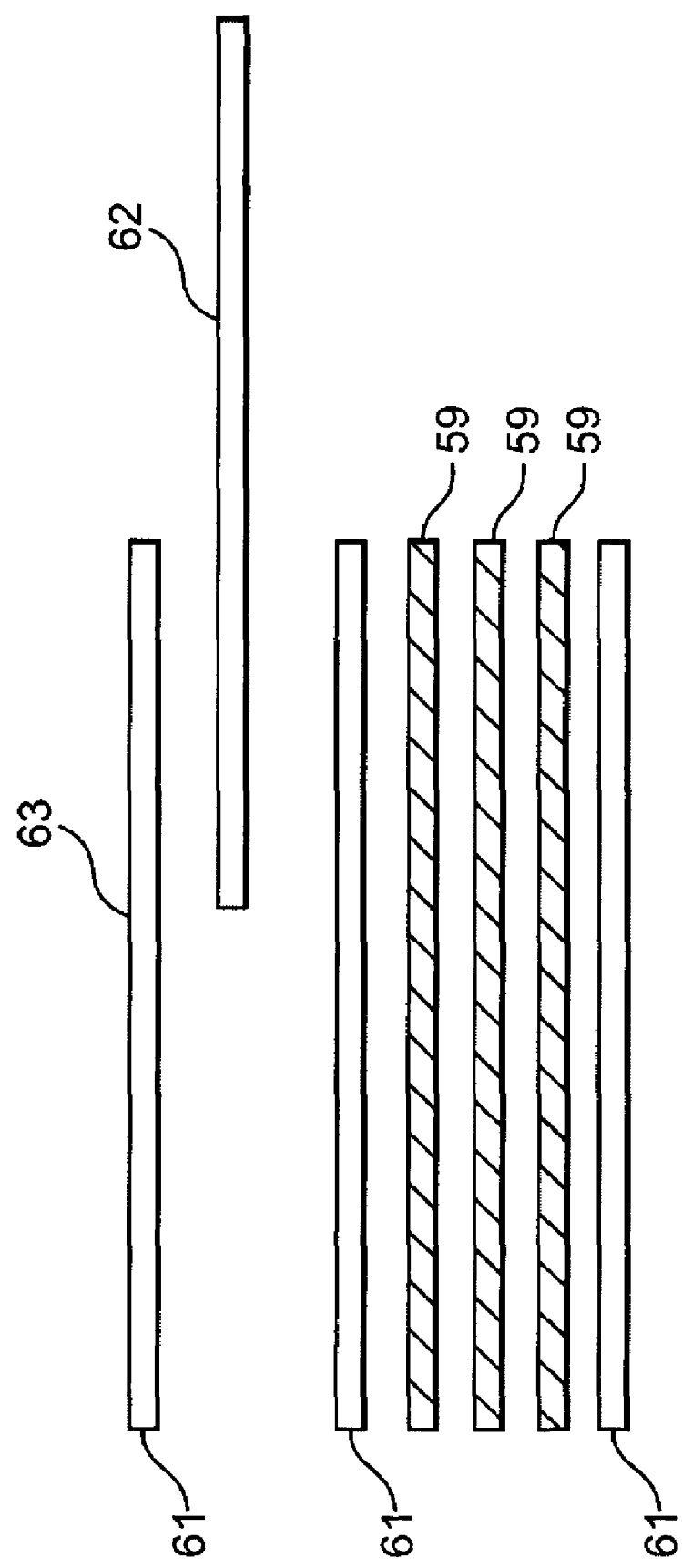
FIG. 4 is a side cross-sectional view the base laminate of FIG. 3.

In FIG. 3 and FIG. 4, construction of internal antenna 54 begins with base laminate 58. Base laminate 58 is constructed of a plurality of layers, preferably three layers, of Metglas™ material 59 secured together by a suitable adhesive, such as Pyralux® acrylic adhesive. Each layer of Metglas™ material 59 is approximately 0.001 inch (0.0254 millimeters) thick. Eight eddy current grooves 60 are radially etched by laser into one side of the layers of Metglas™ material 59 at approximately equal radial spacings. An insulative layer of polyimide is adhesively secured to each side of Metglas™ laminate resulting in a base laminate 58 approximately 0.15 inches (3.8 millimeters) thick. Base laminate 58 is approximately 1.54 inches (39 millimeters) square with two rounded corners to facilitate subsequent assembly.

Figure 5:
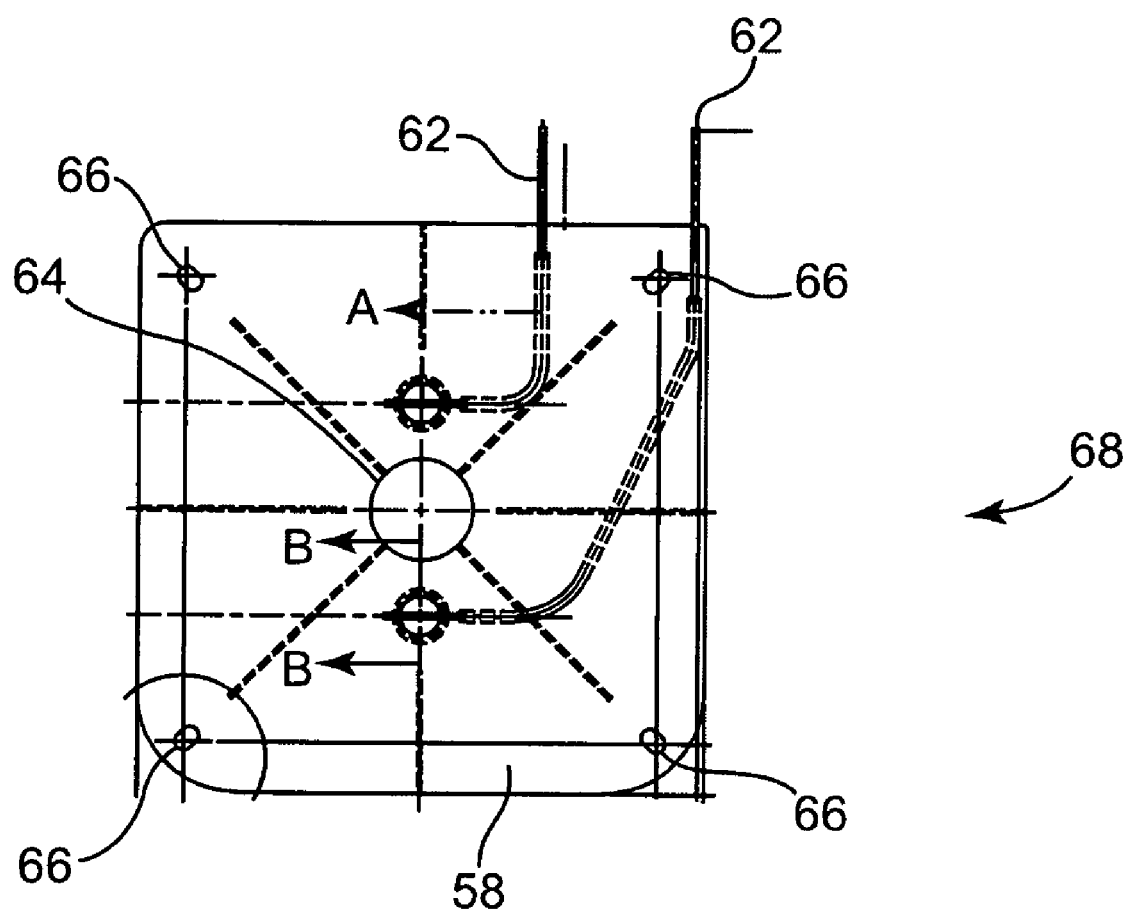
FIG. 5 is a top view of coil ready coreless laminate formed from the base laminate of FIGS. 3 and 4.

Lead wires 62 are placed (FIG. 5) onto base laminate 58 with ends positioned at locations adapted to connect with wires from a coil to added to base laminate 58. Lead wires 62 are placed inboard and, generally, away from cutouts for hub 64 and feet 66. Preferably, lead wires 62 are flat 0.004 inch (0.10 millimeters) and round 0.015 inch (0.38 millimeters) in locations 70 and 72 exiting base laminate 58. Preferably, lead wires 62 are made from niobium ribbon wire. Once positioned, lead wires 62 are secured in place by adhesively securing another layer 63 of polyimide to the side of base laminate 58 onto which lead wires 62 have been positioned. The resulting structure forms a coil ready coreless laminate 68 ready to receive a coil of wire that forms secondary coil 34. Pre-placing lead wires 62 onto base laminate 58 reduces stress from normal movement of lead wires 62 and aids in further assembly.

Prior to being placed onto the surface of coil ready coreless laminate 68, secondary coil 34 is preferably coated in a siloxane coating process. Secondary coil 34 is placed in a vacuum chamber that is then evacuated to 0.10 torr vacuum and held for ten (10) minutes. 10 sccm of Hexamethyldisiloxane, 30 sccm of Nitrous oxide and 1 sccm of Argon are pumped into the chamber. Approximately 150 watts of power to ignite the plasma for thirty (30) seconds.

Figure 6:
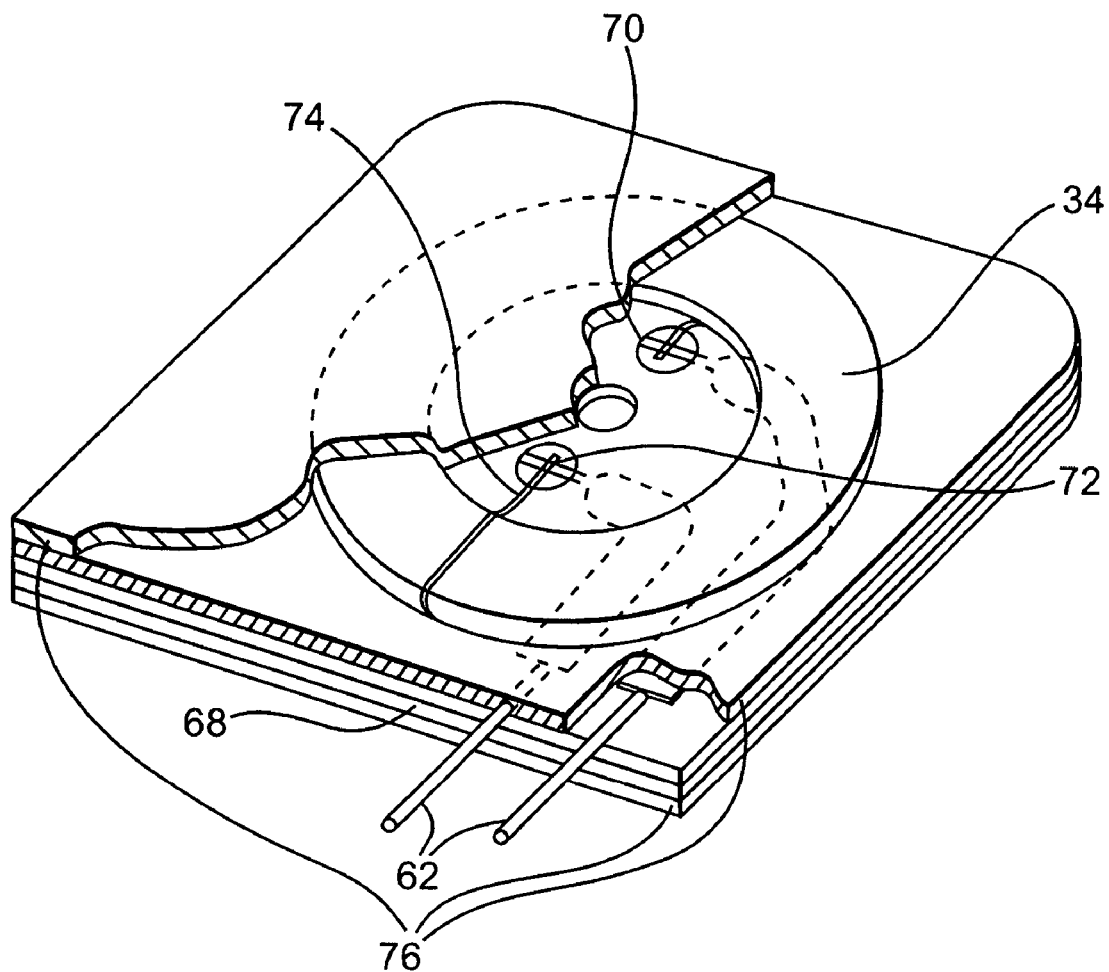
FIG. 6 is an perspective view of the laminate of FIG. 5 having received a secondary charging coil.
Figure 7:
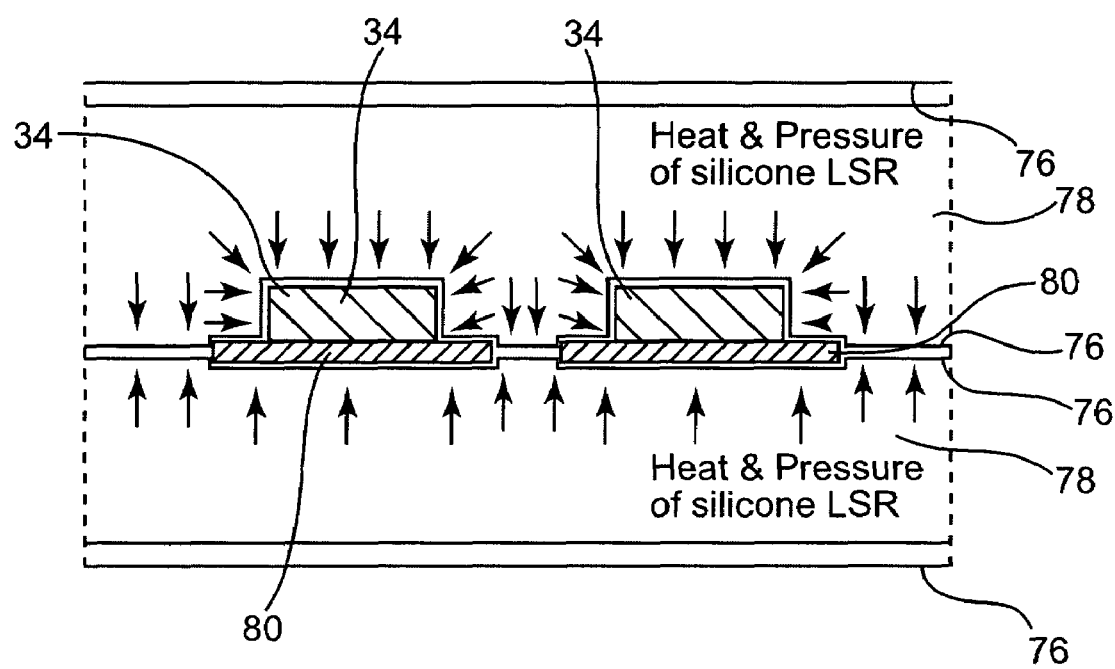
FIG. 7 is an illustration of a pressure lamination process securing cover sheets to the laminated substrate.

In FIG. 6, secondary coil 34 is then placed onto the surface of coil ready coreless laminate 68 and electrically connected to lead wires 62 at locations 70 and 72 by welding or, preferably, opposed welding. Cross-over copper wire 74 from secondary coil 34 makes electrical connection at location 72. The resulting substrate 80 is then sandwiched between a cover sheet 76 of polyimide secured with a thermoset adhesive as illustrated in FIG. 7. Substrate 80 is placed into a press between polyimide cover sheets 76 which, of course, can be added either before or after substrate 80 is placed into the press. A thermoset adhesive, preferably Pyralux® acrylic adhesive, is located between substrate 80 and cover sheets 76. A liquid thermoset polymer, such as liquid silicone rubber, is added to the press outside of cover sheets 76. Heat, preferably approximately 340 degrees Fahrenheit, and pressure, preferably approximately 1,200 pounds per square inch (8,274 pascals), are applied in the press forcing liquid thermoset polymer again cover sheets 76 which are, in turn, pressed against substrate 80. The use of a liquid material in the press allows the press to apply force evenly against the irregular upper surface of substrate 80. The thermoset polymer is allowed to cure under heat and pressure for approximately five (5) minutes forming an at least partially cured silicone rubber sheet on either side of substrate 80 and allowed to cool for approximately twenty (20) minutes. The assembly can then be removed from the mold and the silicone rubber sheets removed (peeled) away and discarded leaving the laminated substrate 80.

This process can increase the efficiency of laminating a plurality of articles. The press is only used during while the liquid thermoset polymer is being pressed to substrate 80. Once the liquid thermoset polymer has cured, e.g., approximately five (5) minutes, the laminated substrate 80 may be removed from the press. The laminated substrate 80 can continue to be allowed to cool outside of the press, e.g., for approximately twenty (20) minutes. As soon as the first laminated substrate 80 is removed from the press, the press may be used again to produce a second laminated substrate 80. Since the laminated substrate 80 need only remain in the press during the initial stages (first five (5) minutes) for curing, the press may be used to produce a second laminated substrate 80 while the first laminated substrate 80 continues to cool. The early re-use of the press, as compared with having to along laminated substrate to remain in the press for the entire cooling time, is a consider savings in equipment time and allows a greatly increased efficiency of operation.

Figure 8:
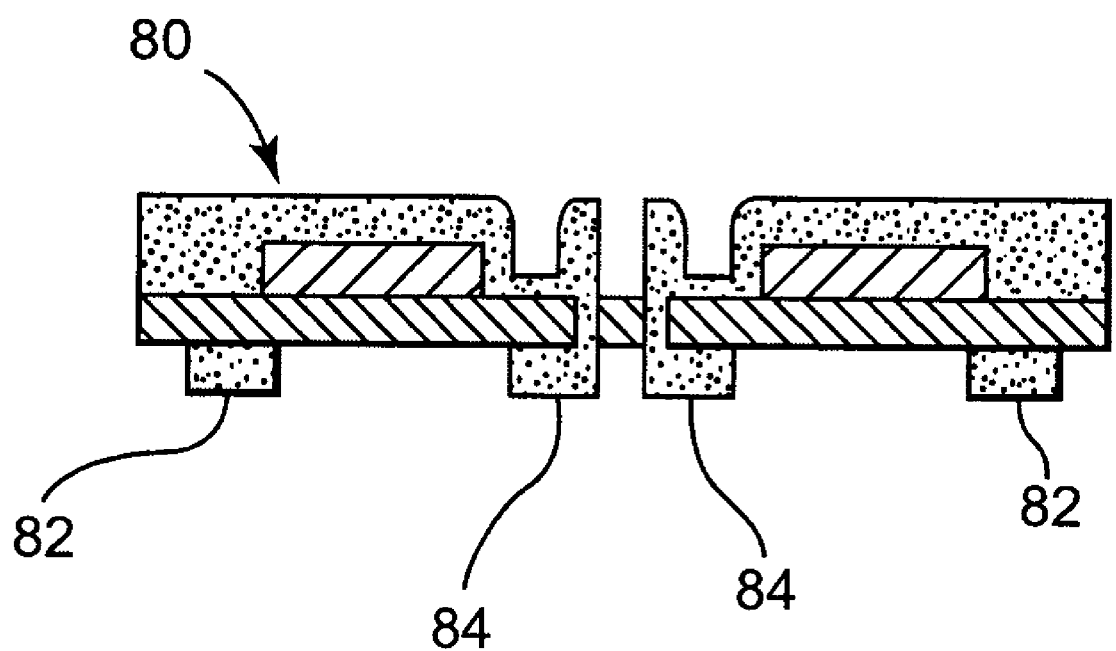
FIG. 8 illustrates the attachment of support feet in a first step in an overmolding process.

Laminated substrate 80 is then overmolded to seal laminated substrate in an environment better able to withstand the harmful effects of bodily fluids after implantation. The overmolding takes place in two steps. In the first step shown in FIG. 8, a plurality of support feet 82 are placed on one side, preferably the underside, of laminated substrate 80. Support feet 82 may be molded onto the underside of laminated substrate 80 using conventional molding techniques. Alternatively, support feet 82 may be adhesively attached, e.g., with glue, may be ultrasonically staked or may be otherwise mechanically attached, e.g., by threaded fastener. Support feet 82 may be equally spaced somewhat near each of the four corners of laminated substrate 80. In a preferred embodiment, support feet have a circular cross-section. Preferably hub 84 is also molded, or otherwise mechanically attached, to laminated substrate surrounding a central hole in laminated substrate.

Figure 9A:
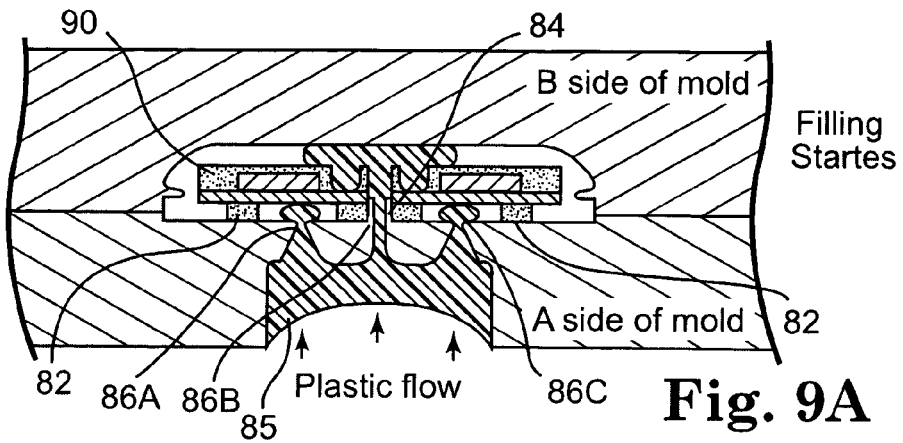
FIGS. 9A, 9B, 9C, 9D and 9E illustrate the injection molding of a second step in an overmolding process.
Figure 9B:
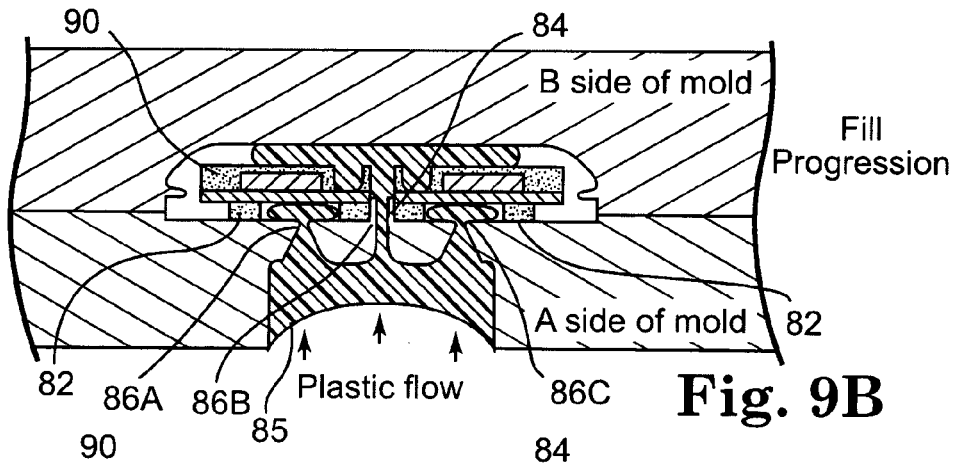
Figure 9C:
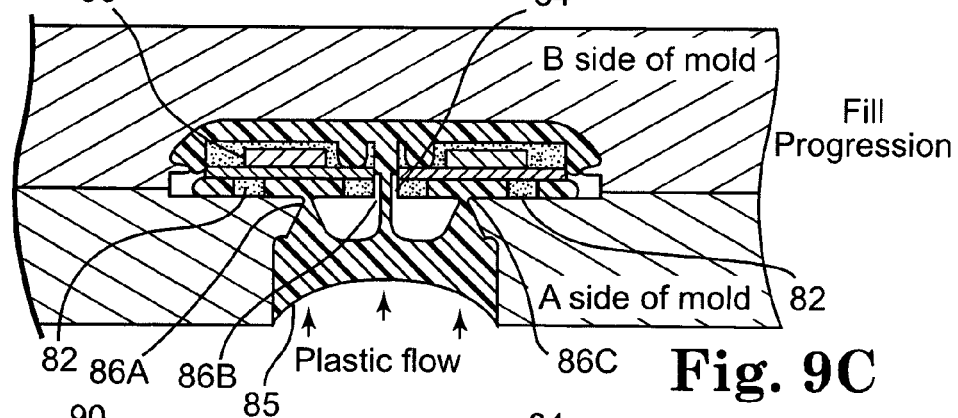
Figure 9D:
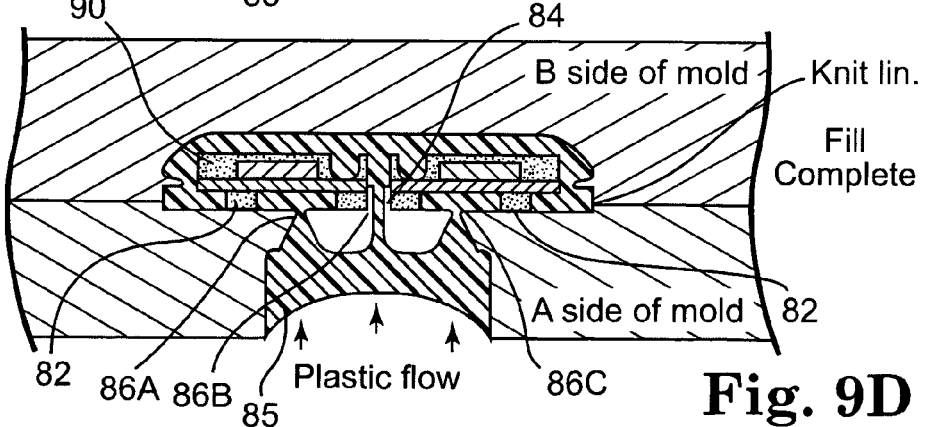
Figure 9E:
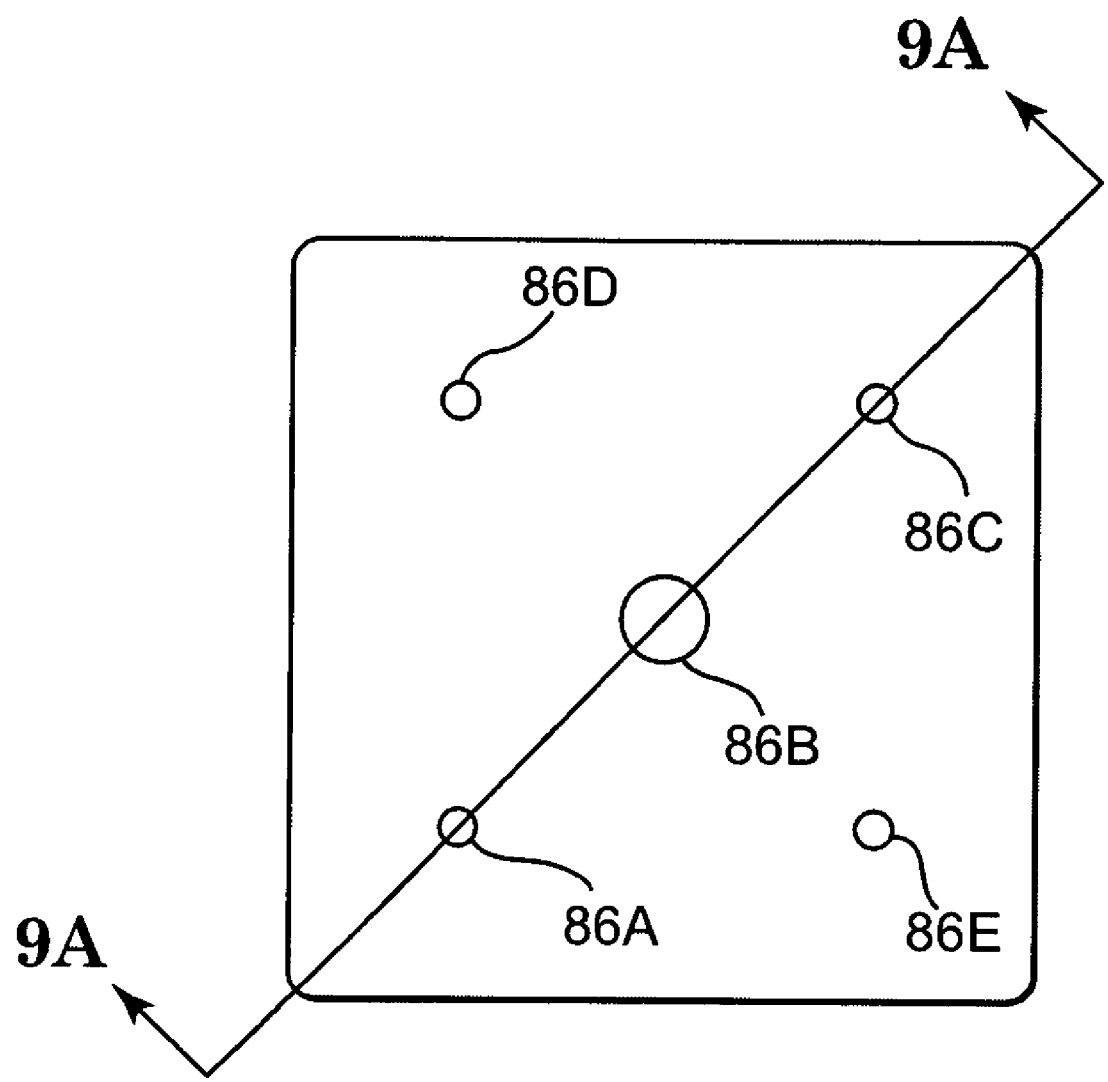

The second part of the overmolding process is illustrated in FIGS. 9A, 9B, 9C and 9D. In FIG. 9A, laminated substrate 90 with support feet 82 and hub 84 is placed into an injection mold. Injection material 85, preferably polysulfone, is introduced into the mold through five (5) injection holes (86A, 86B, 86C, 86D and 86E) from one side of the injection mold. Please note that the FIGS. 9A, 9B, 9C and 9D represent a cross-sectional view of the injection mold. Although a total of five (5) injection holes are utilized, only three (3) are visible in the cross-sectional view. One (1) injection hole is used for the hub (injection hole 86B). Four (4) injection holes are equally spaced as illustrated in FIG. 9E. Note that injection holes 86D and 86E are not visible in the cross-sectional view in FIG. 9A. Injection material 85 begins to flow into the underside of laminated substrate 80 through injection holes 86A and 86C. Injection material 85 also begins to flow through hub 84 and spreads out over the topside of laminated substrate 80 through injection hole 86B. In FIG. 9B, injection material 85 continues to flow into the injection mold through the five (5) injection holes (86A, 86B, 86C, 86D and 86E) in a manner such that the amount of injection material 85 flowing over the topside of laminated substrate 80 and the amount of injection material 85 flowing over the underside of laminated substrate 80 is such that mechanical forces against laminated substrate 80 are evened out from topside and underside. Generally, this is expected to occur when injection material 85 flows at approximately the same rate over the topside of laminated substrate 80 as over the underside of laminated substrate 90. That is, injection material 85 on the topside of laminated substrate 80 is forcing against the topside of laminated substrate 80 with about the same amount of force that injection material 85 is forcing against the underside of laminated substrate 80. The general evening of molding forces for topside to underside helps stabilize laminated substrate 80 during the molding process and helps to eliminate warping of laminated substrate 80. In FIG. 9C, injection material 85 continues to flow evenly over the topside and the underside of laminated substrate 80. In FIG. 9D, injection material 85 has filled the injection mold essentially filling all of the cavity of the injection mold resulting in an overmolded laminated substrate 80. Injection holes 86A, 86B, 86C, 86D and 86E are chosen in size such to facilitate the even flow of injection material 85. If injection material 85 does not flow evenly over both the topside and the underside of laminated substrate 80, the resultant overmolded part can warp following cooling.

As shown in FIGS. 9A, 9B, 9C and 9D, injection material 85 flows around support feet 82 and encircles each of circular support feet 82. As injection material 85 cools following the injection molding process, injection material 85 has a tendency to shrink. Typically, shrinkage of injection material may create a crack or a gap which may create an area into which bodily fluids could subsequently gain entry following implantation. However, by encircling each of support feet 82, such shrinkage of injection material 85 will actually cause injection material to form more tightly around support feet 82 creating an even stronger bond and helping to ensure that bodily fluids can not gain entry following implantation. This same technique holds true for hub 84. Hub 84 has a circular cross-section and has surrounding a indentation which allow injection material 85 to surround hub 84 and shrink more tightly to hub 84 as injection material 85 cools creating a stronger bond and less likelihood of leaks.

Figure 10:
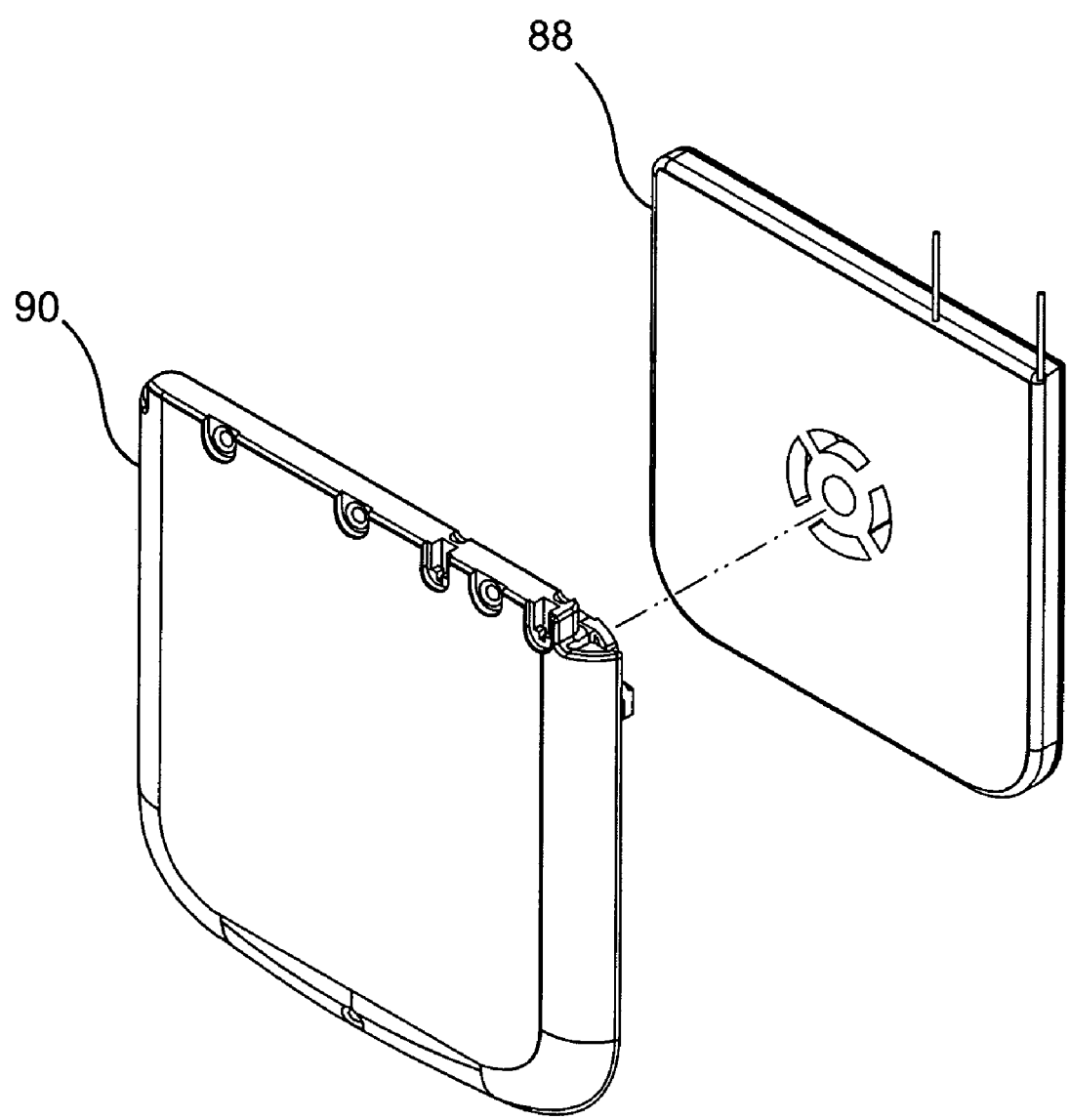
FIG. 10 is an exploded view of an internal antenna showing both the overmolded laminated substrate and a cover.
Figure 11:
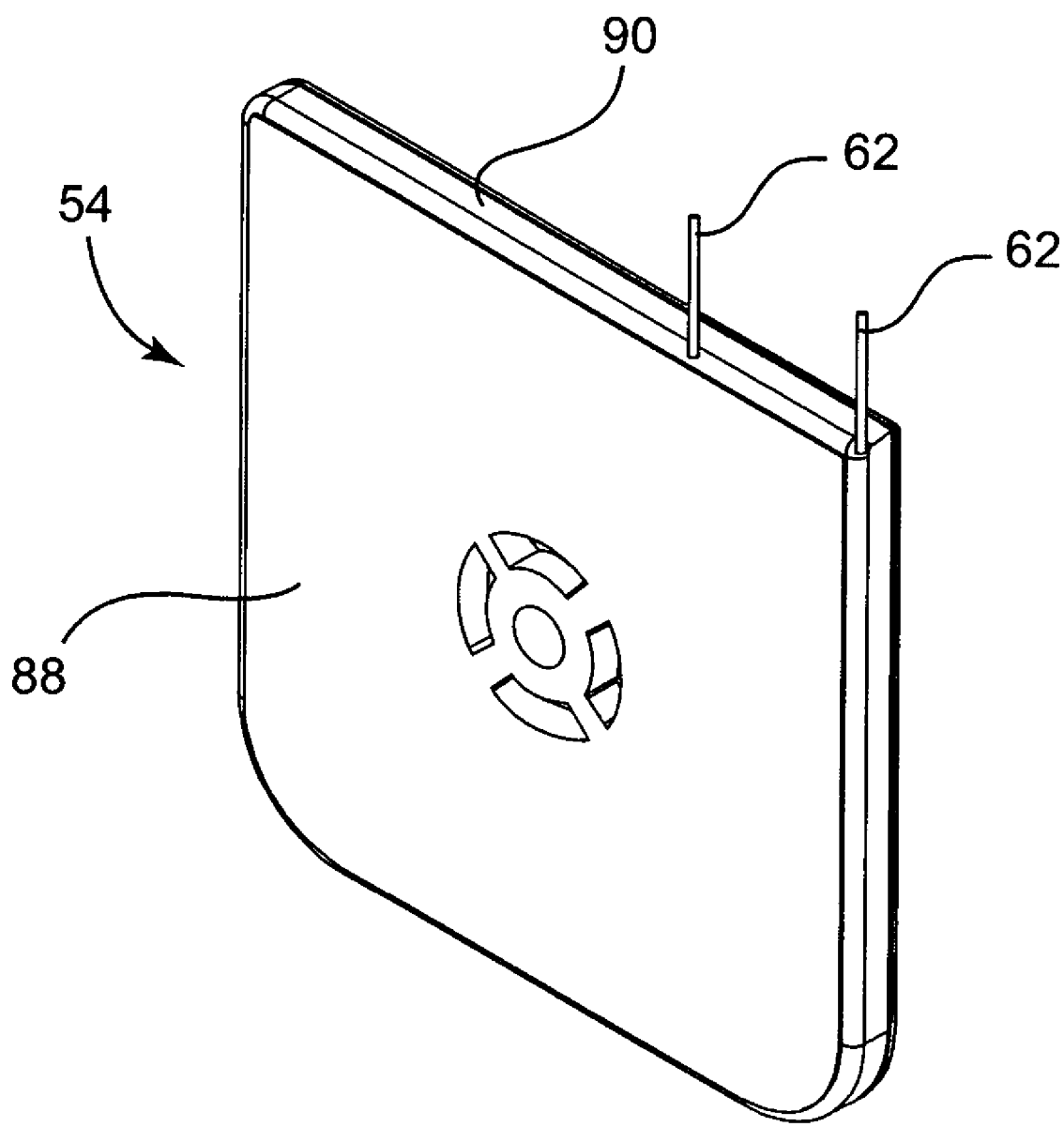
FIG. 11 is a perspective view of an internal antenna for use with an implantable medical device.

Overmolded cover 90, created in FIGS. 9A, 9B, 9C and 9D, by overmolding laminated substrate 88 in an injection mold, is shown in FIG. 10 with polysulfone cover 85. Cover 90 is mechanically joined with overmolded substrate 88 in a conventional manner to complete the assembly of internal 54 (shown in FIG. 11).

Figure 12:
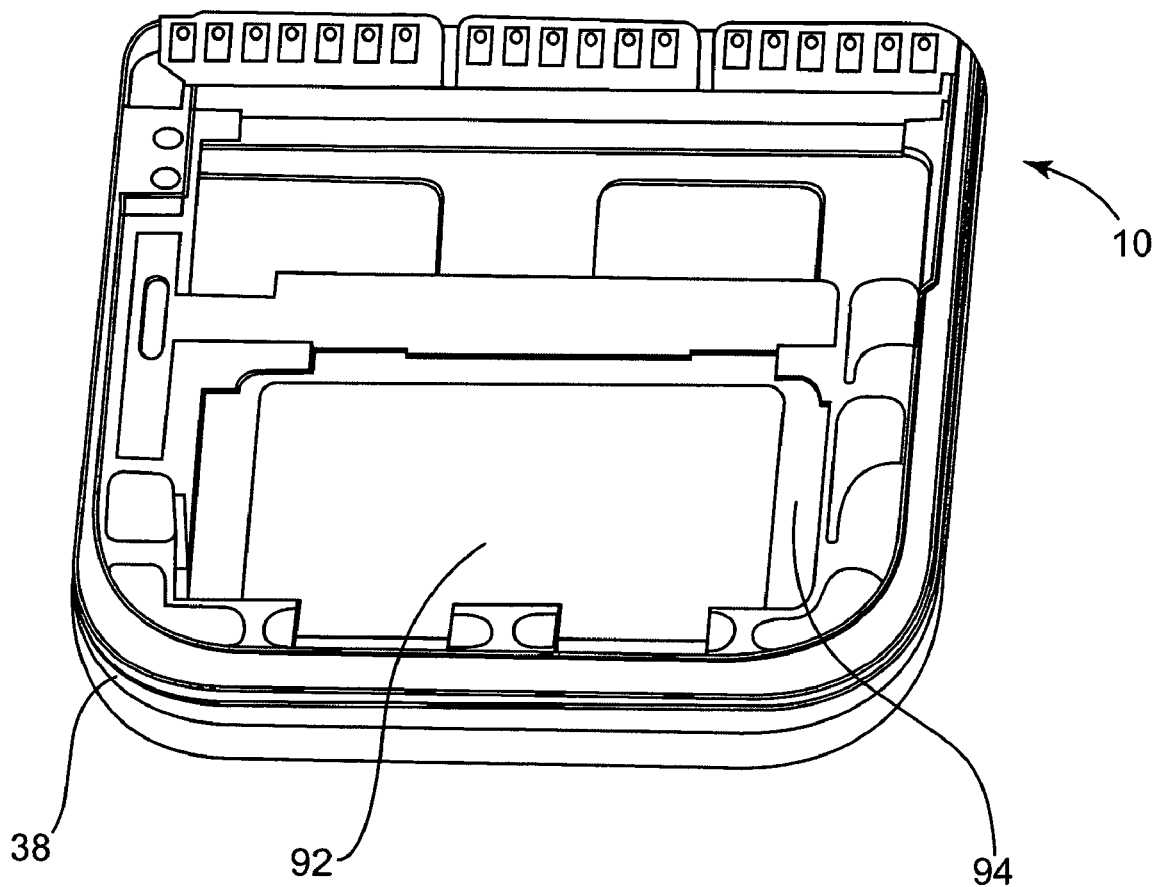
FIG. 12 illustrates an interior view of a housing of an implantable medical device showing the positioning of a power source.
Figure 14:
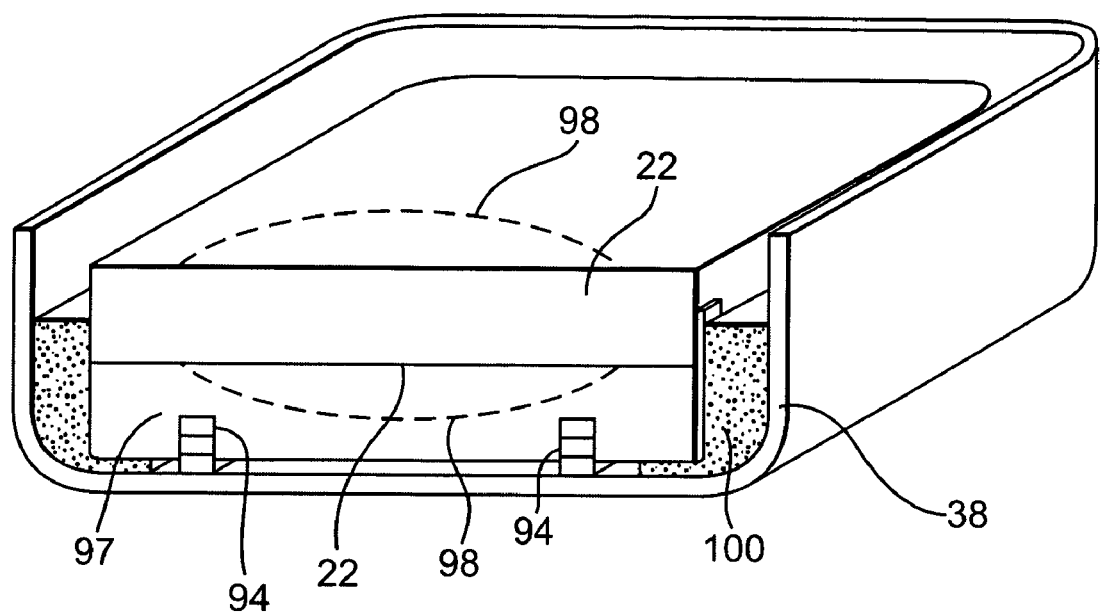
FIG. 14 is a cross-sectional view of an implantable medical device showing the placement and support of a battery.
Figure 13:
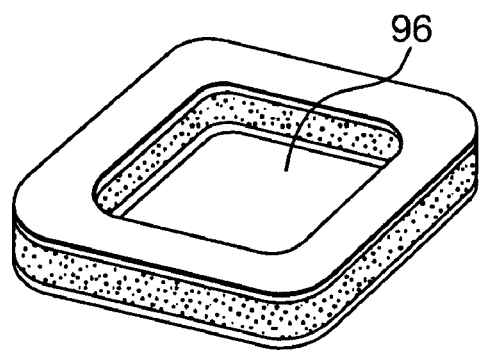
FIG. 13 is a perspective view of a battery support for an implantable medical device.
Figure 15:
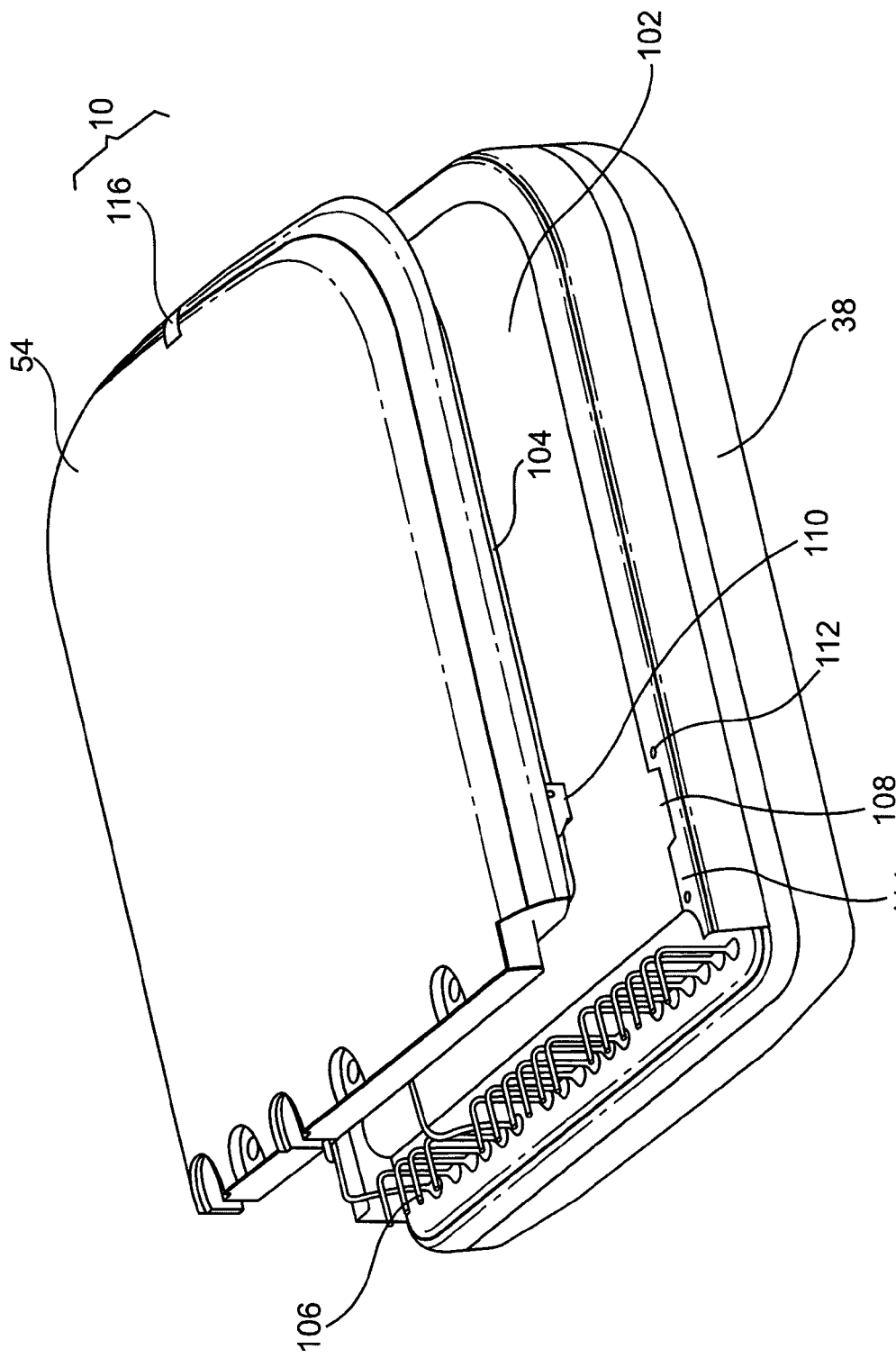
FIG. 15 is a perspective view an internal antenna about to be mated with a housing of implantable medical device.
Figure 16:
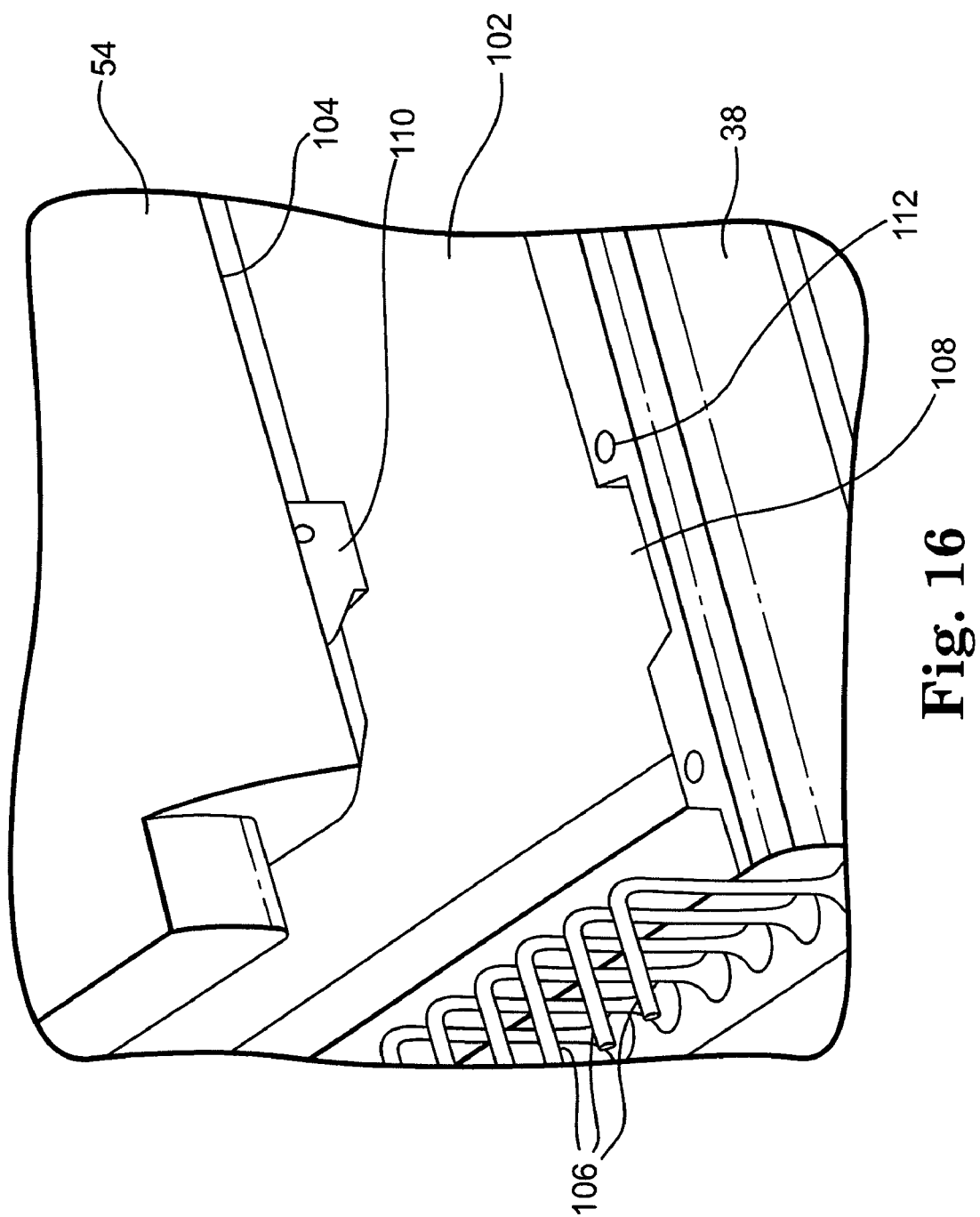
FIG. 16 is a detailed view of a portion of FIG. 15 illustrating an engagement tab.
Figure 19:
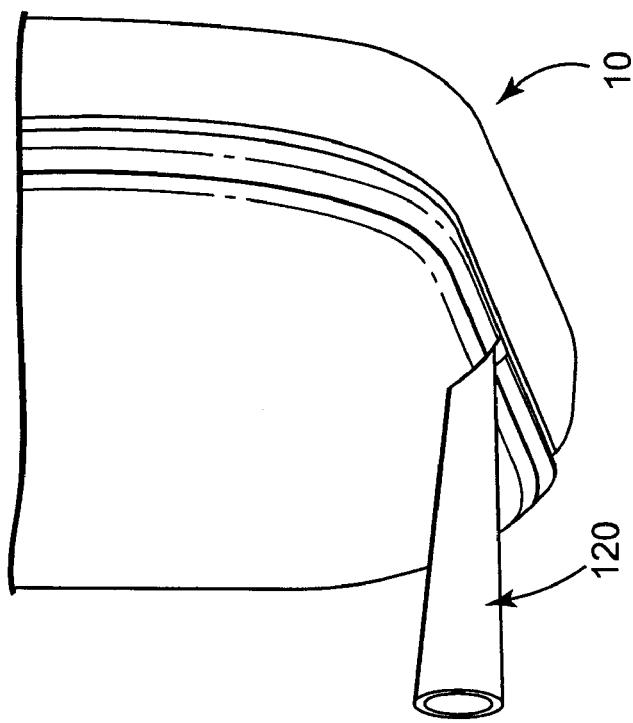
FIG. 19 is a detailed view of internal antenna mounted to housing illustrating sealing implantable medical device using an adhesive needle.
Figure 20:
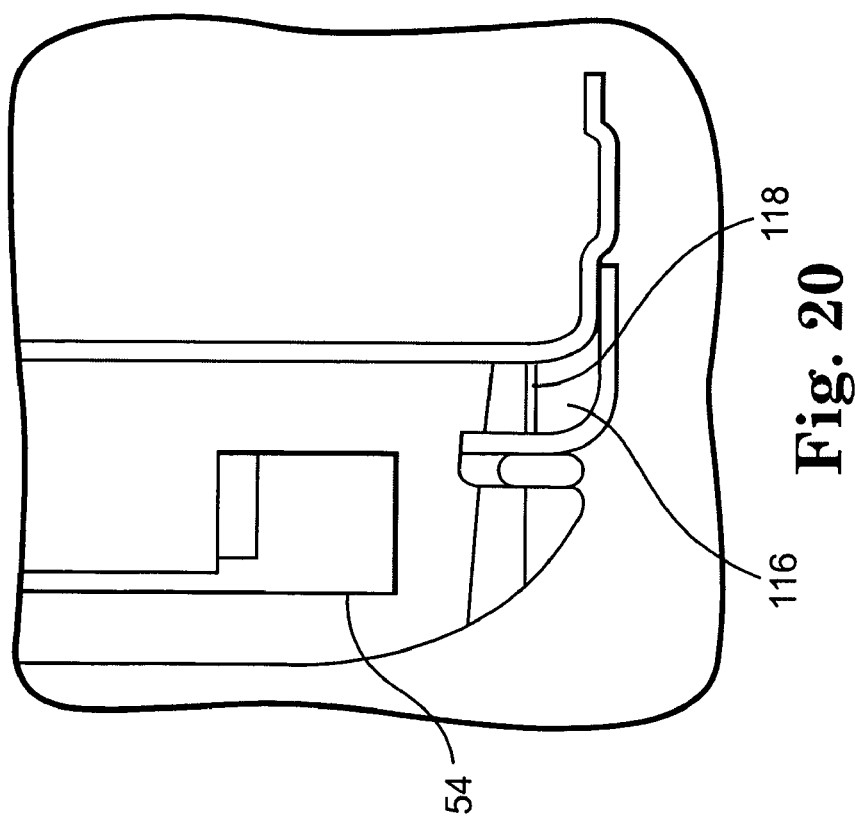
FIG. 20 is a cross-sectional view of a portion of internal antenna and housing illustrating a flow channel for an adhesive sealant.
Figure 21:
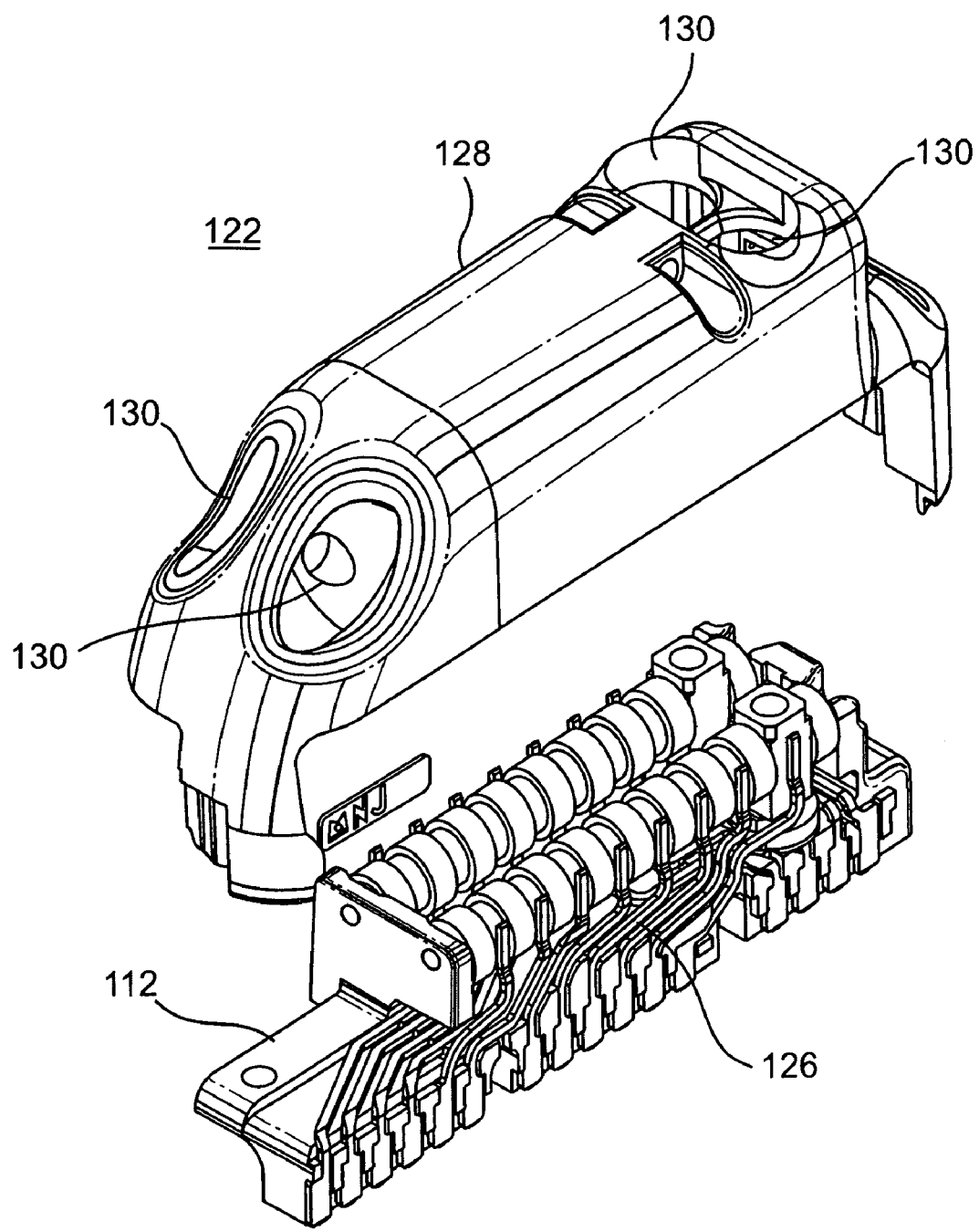
FIG. 21 is an exploded view of a connector block for use with an implantable medical device.
Figure 23:
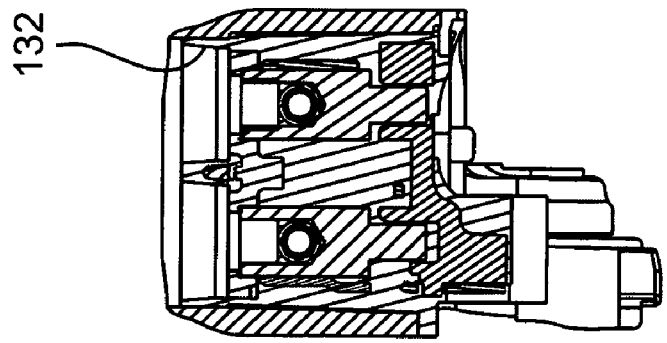
FIG. 23 is a partial cross-section view of the connector block of FIG. 21 illustrating a chimney.
Figure 22:
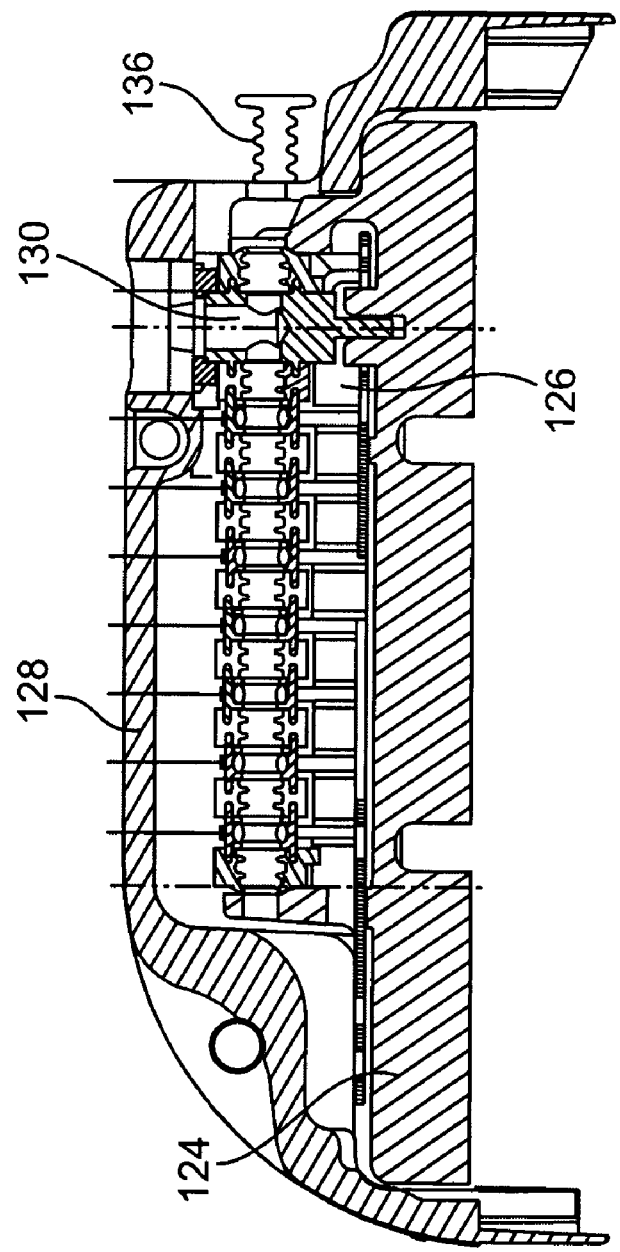
FIG. 22 is a cross-sectional view of the connector block of FIG. 21.
Figure 24:
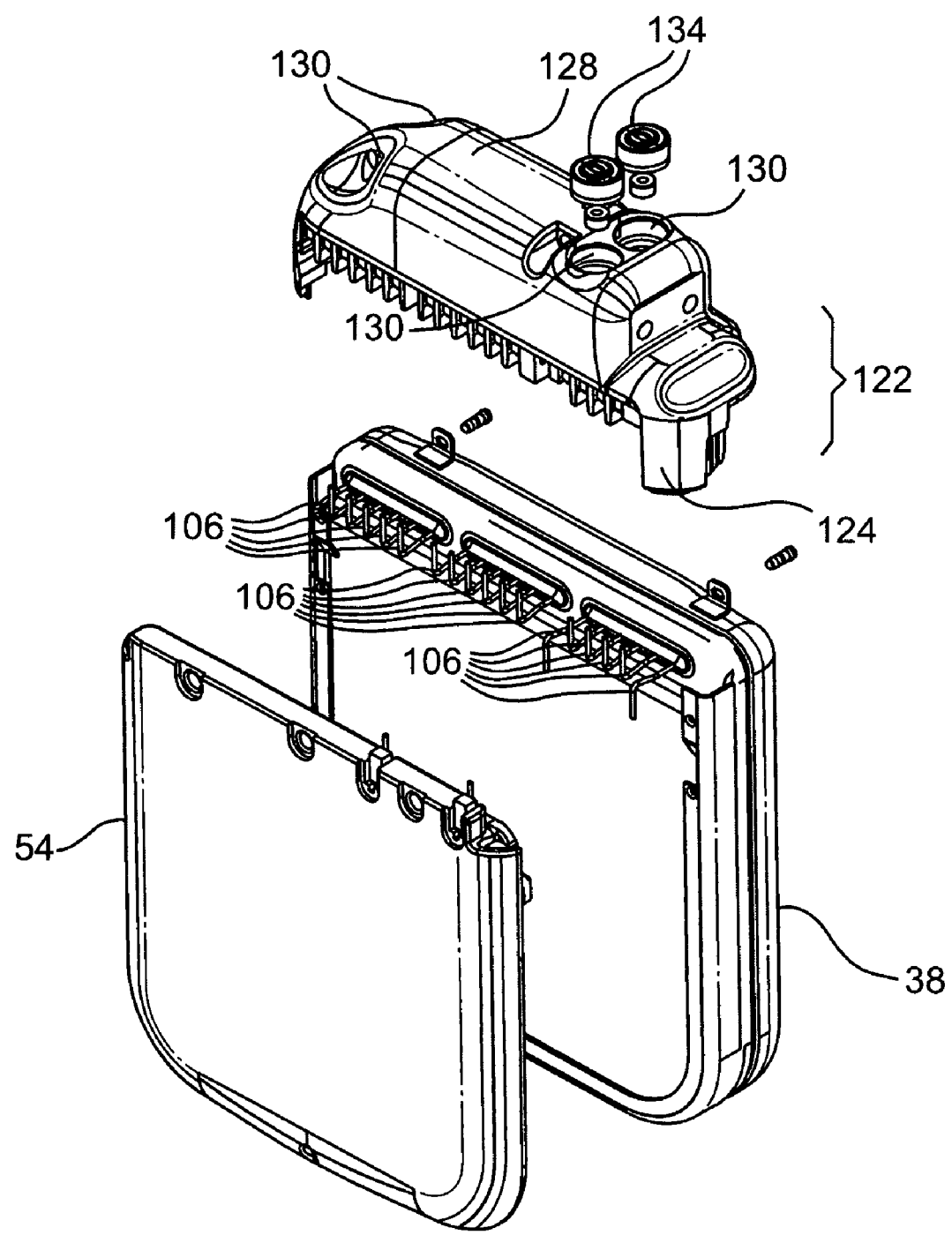
FIG. 24 is an exploded view illustrating the assembly of internal antenna, housing and connector block of implantable medical device.

FIG. 12 shows housing 38 of portion of implantable medical device 10 holding power source 22, electronics module 24 and other components. Power source (preferably a battery) 22 is located in area 92 in housing 38. It is desirable that battery 22 be reasonably secured within housing 38 but at the same be allowed to expand and contract with use. Chemical batteries, such as battery 22, may have a tendency to expand as the battery 22 is charged and subsequently contract as the battery 22 ceases to be charged. Such expansion and contraction in a battery 22 which is very tightly secured in housing 38 might cause battery 22 to either come loose from its attachments and/or compromise its electrical connections. Therefore, in a preferred embodiment battery 22 is held in a manner which allows battery 22 to expand, e.g., during charging, and subsequently contract, e.g., following charging, without compromising mechanical and/or electrical connections. Spacer 94, seen more clearly in FIG. 13, supports battery 22 around the periphery of battery 22 while cutout 96 in the central portion of spacer 94 allows battery 22 to expand without compromise. In a preferred embodiment, battery 22 has a rectangular shape with major and minor sides. Preferably, spacer 94 supports a major side of battery 22 while allowing cutout 96 to allow expansion of the major side of battery 22. In a preferred embodiment, spacer 94 is constructed with a layer of polyimide approximately 0.001 inch (0.0254 millimeters) thick. Preferably, spacer 94 is secured in an inside surface of housing 38 with a suitable adhesive (see FIG. 14). As can be seen in FIG. 14, battery 22, fits inside battery cup 97 supported by spacer 94, is allowed to expand, e.g., during charge, as illustrated by expansion dotted lines 98. During a subsequent operation of assembly of implantable medical device 10, epoxy 100 is introduced into housing 38 to help secure battery 22. Battery cup 97 and spacer 94 will help to ensure that epoxy 100 does not fill the space created by spacer 94.

FIGS. 15 through 20 illustrate the mechanical connection of internal antenna 54 to housing 38 to achieve an integrated implantable medical device 10 that will be able to withstand the ravages of bodily fluids once implanted. Housing 38 has a recharge rail 102 extending around three sides that is adapted to slideably mate with a complementary rail 104 on internal antenna 54. However, electrical connector wires 106 inhibit rail 104 of internal antenna 54 from engaging recharge rail 102 from the open end. While electrical connector wires could be bent and then reformed to the illustrated position following installation of internal antenna 54 onto housing 38, this is not desirable from a reliability standpoint, due to the bending and straightening of wires 106, it is also inefficient. Recharge rail 102 has a drop opening 108 allowing tab 110 of internal antenna 54 to drop into opening 108 and then allow rail 104 to slidably engage recharge rail 102 which are configured to slidably engage over a portion of the sliding distance. This "drop and slide" engagement allows internal antenna 54 to drop avoiding interference with electrical connection wires 106 and still slidably securely engage to housing 38. Detent 112 provides tactile feedback to the installer to know when proper sliding engagement is achieved. Following engagement, locking tab 114 may be purposely bent up to engage the rear of rail 104 preventing internal antenna 54 from disengaging with housing 38. It is to be recognized and understood that all of these engaging and locking mechanisms preferably exist on both sides of implantable medical device 10 in complementary fashion even though the drawings illustrate only one side.

An adhesive channel 116 is formed around the perimeter of housing 38. Fill hole 118 communicates through both internal antenna 54 and housing 38 to allow an adhesive needle 120 to be inserted. Adhesive needle 120 may then be used to fill adhesive channel 116, through fill hole 118, with adhesive providing another layer of sealing for implantable medical device 10.

Once internal antenna 54 is secured to housing 54, electrical connector wires 106 may be connected using connector block 122 as shown in FIGS. 21, 22, 23 and 24. Rigid polysulfone frame 124 provides structural rigidity to connector block 122. Frame 124 is laid out in linear fashion so that all electrical connections are in a linear row. Wire frame 126 is stamped out of a conductive material, preferably a metal. Since rigid frame 124 is laid out linearly, wire frame 126 can be stamped with a plurality of linear connector areas. Wire frame 126 is joined with rigid frame 124 and mated with electrical connector wires 106. Frame cover 128 fits over rigid frame 124. Once assembled, a biocompatible thermoset polymer, such as silicone rubber, can be injected into connector block 122 substantially filling any voids in connector block 122 forming a thermoset polymer gasket helping to prevent infiltration of body fluids into implantable medical device 10. The thermoset polymer (not shown) also provides electrical isolation between the electrical contacts of wire frame 126.

Connector block 122 has a plurality of openings 130 allowing an external electrical connection with implantable medical device 10. Chimneys 132 form a void near the external electrical contact openings allowing the thermoset polymer to at least partially fill chimney 132 to further seal and secure an electrical connection opening into implantable medical device 10. Such thermoset polymer also provides a strain relief for the lead used for the external electrical connection. Grommets 134, which are compatible with thermoset polymer, additionally secure and electrically isolate the external electrical connection. A set screw 136 may be used to mechanically secure the external wire to connector block 122. As thermoset polymer substantially fills voids within connector block 122, thermoset polymer forms a skirt, when cured, that is usually thinner than is reasonably possible to be created with rigid frame 124 or thermoplastic cover 128. The thinner skirt achieved with the thermoset polymer allows an even stronger and more secure seal against the intrusion of body fluids.

In a preferred embodiment, rigid frame is treated before assembly with an adhesion promoter to create a stronger bond between rigid frame 124 and thermoset polymer. The surface of polysulfone rigid frame 124 is cleaned with a detergent, preferably Micro 90™ detergent, rinsed first in D.I. water and then rinsed in IPA. Polysulfone rigid frame 124 is plasma treated by first being placed in a vacuum chamber that is then evacuated to 0.10 torr vacuum and held for ten (10) minutes. 10 sccm of Hexamethyldisiloxane, 30 sccm of Nitrous oxide and 1 sccm of Argon are pumped into the chamber. Approximately 150 watts of power to ignite the plasma for thirty (30) seconds. Rigid frame 124 is then coated by being dipped into a twenty percent (20%) solution of RTV medical silicone adhesive and heptane by weight for approximately two (2) seconds. Rigid frame 124 is then removed from the dip and cured in an oven at 150 degrees Centigrade for eight (8) hours.

Thus, embodiments of the connector block for an implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A laminate, comprising:
   a plurality of layers of magnetic material sandwiched together having a first side and a second side;
   said plurality of layers of magnetic material having a plurality of radial grooves;
   a first insulative layer applied over said first side of said plurality of layers of magnetic material;
   a lead wire applied to over first insulative layer at a predetermined location on said first side of said plurality of layers of magnetic material;
   a second insulative layer applied to said first side of said plurality of layers of magnetic material over said lead wire; and
   a third insulative layer applied to said second side of said plurality of layers of magnetic material;
   whereby said laminate is ready to receive a coil.

2. A laminate as in claim 1 wherein each of said first insulative layer, said second insulative layer and said third insulative layer comprises a polymer.

3. A laminate as in claim 2 wherein said polymer comprises polyimide.

4. A laminate as in claim 1 wherein said third insulative layer is adhesively applied.

5. A laminate as in claim 1 wherein said plurality of layers of magnetic material are sandwiched together with intervening adhesive layers.

6. A laminate as in claim 1 wherein said lead wire is adhesively applied.

7. A laminate as in claim 1 wherein said second insulative layer is adhesively applied to said first side of said first insulative layer over said lead wire.

8. A laminate as in claim 1 wherein said plurality of layer of magnetic material comprises three layers.

9. A laminate as in claim 1 wherein said predetermined location is selected to accommodate connection with said coil.

10. A laminate as in claim 1 further comprising a second lead wire applied at a second predetermined location on said first side of said plurality of layers of magnetic material.

11. A laminate as in claim 10 wherein said second predetermined location is selected to accommodate connection with said coil.

12. A method of making a laminate, comprising the steps of:

sandwiching together a plurality of layers of magnetic material, said plurality of layers of magnetic material having a first side and a second side;

creating a plurality of radial grooves in said plurality of layers of magnetic material;

applying a first insulative layer over said first side of said plurality of layers of magnetic material;

applying a lead wire over said first insulative layer at a predetermined location on said first side of said plurality of layers of magnetic material;

applying a second insulative layer to said first side of said plurality of layers of magnetic material over said lead wire; and whereby said laminate is ready to receive a coil.

13. A method as in claim 12 further comprising the step of applying a third insulative layer to said second side of said plurality of layers of magnetic material.

14. A method as in claim 13 wherein each of said first insulative layer, said second insulative layer and said third insulative layer comprises a polymer.

15. A method as in claim 14 wherein said polymer comprises polyimide.

16. A method as in claim 12 wherein said sandwiching together step comprises adhesively securing said plurality of layers of magnetic material together.

17. A method as in claim 12 wherein said applying said lead wire step comprises adhesively securing said lead wire.

18. A method as in claim 12 wherein said applying said second insulative layer step comprises adhesively securing said second insulative layer to said first insulative layer over said lead wire.

19. A method as in claim 12 wherein said applying said third insulative layer step comprises adhesively securing said third insulative layer to said second side of said plurality of layers of polymer.

20. A method as in claim 12 wherein said plurality of layer of magnetic material comprises three layers.

21. A method as in claim 12 wherein said predetermined location is selected to accommodate connection with said coil.

22. A method as in claim 12 further comprising the step of applying a second lead wire at a second predetermined location on said first side of said plurality of layers of magnetic material.

23. A method as in claim 22 wherein said second predetermined location is selected to accommodate connection with said coil.

* * * * *